US005545184A

United States Patent [19]
Dougherty

[11] Patent Number: 5,545,184
[45] Date of Patent: Aug. 13, 1996

[54] CARDIAC DEFIBRILLATOR WITH HIGH ENERGY STORAGE ANTIFERROELECTRIC CAPACITOR

[75] Inventor: Joseph P. Dougherty, State College, Pa.

[73] Assignee: The Penn State Research Foundation, University Park, Pa.

[21] Appl. No.: 423,500

[22] Filed: Apr. 19, 1995

[51] Int. Cl.$^6$ ........................................... A61N 1/39
[52] U.S. Cl. ........................................... 607/5
[58] Field of Search ............... 607/5, 7, 34; 252/62.9; 361/313, 320, 321.4, 321.5; 501/134, 135

[56] References Cited

U.S. PATENT DOCUMENTS

| | | | |
|---|---|---|---|
| 3,569,822 | 3/1971 | Neilson et al. | 323/93 |
| 3,917,780 | 11/1975 | Mazdiyasni et al. | 264/61 |
| 4,027,209 | 5/1977 | Maher | 361/361 |
| 4,135,224 | 1/1979 | Maher | 361/321 |
| 4,219,866 | 8/1980 | Maher | 361/321 |
| 4,254,775 | 3/1981 | Langer | 128/419 D |
| 4,324,750 | 4/1982 | Maher | 264/61 |
| 4,396,721 | 8/1983 | Lawless | 501/10 |
| 4,461,844 | 7/1984 | Itakura et al. | 501/137 |
| 4,580,191 | 4/1986 | Cansell et al. | 361/323 |
| 4,706,163 | 11/1987 | Maher | 361/321 |
| 4,712,156 | 12/1987 | Bardhan | 361/321 |
| 4,832,893 | 5/1989 | Hisanaga et al. | 364/125 |
| 4,843,046 | 6/1989 | Yamaguchi et al. | 501/136 |
| 4,885,267 | 12/1989 | Takahara et al. | 501/134 |
| 4,942,501 | 7/1990 | MacFarlane et al. | 361/523 |
| 4,945,449 | 7/1990 | Cansell et al. | 361/273 |
| 4,990,324 | 2/1991 | Tomita et al. | 423/608 |
| 5,023,032 | 6/1991 | Bailey et al. | 264/63 |
| 5,079,199 | 1/1992 | Ochi et al. | 501/135 |
| 5,086,374 | 2/1992 | MacFarlane et al. | 361/525 |
| 5,116,643 | 5/1992 | Miller et al. | 427/126.3 |
| 5,131,388 | 7/1992 | Pless et al. | 128/419 D |
| 5,139,689 | 8/1992 | Kitoh et al. | 252/62.9 |
| 5,146,391 | 9/1992 | MacFarlane et al. | 361/525 |
| 5,153,820 | 10/1992 | MacFarlane et al. | 361/525 |
| 5,163,427 | 11/1992 | Keimel | 607/5 |
| 5,164,349 | 11/1992 | Fujii et al. | 501/134 |
| 5,265,588 | 11/1993 | Nelson et al. | 128/419 |
| 5,418,389 | 5/1995 | Watanabe | 501/134 |
| 5,453,262 | 9/1995 | Dawson et al. | 501/134 |

OTHER PUBLICATIONS

ICD: Bridge to Transplant, Author: Jeevanadam et al., Supplement II Circulation vol. 86, No. 5, Nov. 1992, pp. 276–279.

"Proceedings of a Symposium on High–Energy–Density Capacitors and Dielectric Materials", C. Reed, Prepared for Sandia Laboratories by the High–Energy–Density Capacitors and Dielectric Materials Comm. 1981.

"Evolution, Evaluation, and Efficacy of Implantable Cardioverter–Defibrillator Technology" Author: Myerburg et al., Circulation vol. 86, No. 2, Aug. 1992.

The American Journal of Cardiology, vol. 67, Jun. 15, 1991 pp. 1424–1427"The Implantable Defibrillator Backlash", R. Fogoros, M.D.

"Ceramic Dielectives and Capacitors" vol. 6, Gordon & Breach Science Publishers (1985) Author: J. M. Herbert, pp. 128–187.

(List continued on next page.)

Primary Examiner—William E. Kamm
Assistant Examiner—George R. Evanisko
Attorney, Agent, or Firm—Thomas J. Monahan

[57] ABSTRACT

A cardiac defibrillator which incorporates the invention hereof includes a multilayer capacitor with a plurality of conductive electrodes and interspersed dielectric layers, each dielectric layer composed of constituents which cause the dielectric layer to exhibit antiferroelectric characteristics. The defibrillator includes a charging circuit for applying to the capacitor an electric field across each dielectric layer that is at least equal to $E_f$, where $E_f$ is a field value that enables the dielectric layer to transition to a ferroelectric phase. A preferred dielectric material comprises lead, lanthanum, zirconium and titanium, all at constituent values which cause the resulting ceramic material to lie within the antiferroelectric region.

8 Claims, 7 Drawing Sheets

OTHER PUBLICATIONS

"Design for a Constant Peak Current Defibrillator" Author: Machin et al. IEEE Transactions on Biomedical Engineering, vol. 37, No. 7, Jul. 1990 pp. 723–730.

"Piezoelectric Ceramics", B. Jaffe, et al., Academic Press, Inc., NY, NY 1971, pp. 173–183.

"Electrical Defibrillation", W. Tacker et al., CRC Press, Inc. Boca Raton, FL, 1980, Chapter 4.

"Antiferroelectric Ceramics with Field–Enforced Transitions: A New Nonlinear Circuit Element", B. Jaffee, Proceedings of the IRE, Aug., 1961.

"A Minimal Model to the Monophasic Defibrillation Pulse", M. Kroll, PACE, vol. 16, Apr., Part I 1993, pp. 769–777.

"Transthroacic Ventricular Defibrillation with Triangular and Trapezoidal Waveforms", J. Schuder et al., Circulation Research, vol. XIX, Oct. 1966, pp. 689–694.

"The Reliability of Multilayer Ceramic Capacitors", G. Shirn et al., Report No. NMAB–400, Grant No. MDA–903–82–C–0434, by The Committer on the Workshop on the Reliability of Multilayer Ceramic Capacitors, for National Materials Advisory Board, Nat'l Academy of Sciences, DC, pp. 49–66.

PLZT 6/95/5. Applied field = 200kV/cm

PLZT 6/90/10. Applied field = 200 kV/cm

FIGURE 12

PLZT 6/90/10

FIGURE 13

CARDIAC DEFIBRILLATOR WITH HIGH ENERGY STORAGE ANTIFERROELECTRIC CAPACITOR

FIELD OF THE INVENTION

This invention relates to cardiac defibrillators and, more particularly, to an implantable cardiac defibrillator employing a high energy density antiferroelectric capacitor.

BACKGROUND OF THE INVENTION

Cardiac defibrillators are implanted in patients suffering from potentially lethal arrhythmias. An implantable defibrillator includes circuity which monitors cardiac activity and decides, based upon the cardiac activity, whether an application is required of defibrillation energy to the heart muscle. If an arrhythmia is detected, pacing or shock therapy may be used to terminate the arrhythmia.

Cardioversion and defibrillation require that a high voltage shock be delivered to the heart muscle. Upon determining a need for such shock treatment, the defibrillator charges a capacitor to a high level, which charge is then delivered as a shock to the heart muscle. The voltage applied across the heart muscle may be as high as 800 volts and the energy applied to the heart muscle is delivered within a very short time period. (e.g. 5 milliseconds).

Early work by Schuder, et al. ("Transthoracic Ventricular Defibrillation with Triangular and Trapezoidal Waveforms", *Circulation Research*, Vol. XIX, October 1966, pp. 689–694) demonstrated that the pulse shape influences the efficacy of defibrillation. The most commonly held theory on the optimization of defibrillation pulse shape is the average current hypothesis, which is an adaptation of simple cardiac stimulation theory. This general theory states that the efficacy of defibrillation is solely dependent upon the average current of the pulse and the duration of the pulse. This theory implies that other parameters of the pulse are not critical. A recent review of this theory is provided in the article by Mark W. Kroll ("A Minimal Model of the Monophasic Defibrillation Pulse" *Pacing and Clinical Electrophysiology*, Vol. 16, Part I, April, 1993, pp. 769–777). A more complete review of the influence of pulse shape is provided by W. A. Tacker and Leslie A. Geddes in *Electrical Defibrillation* (CRC Press, Inc., Boca Raton, Fla., 1980 (Chapter 4)). Based on this theory and the results of these and other published experiments, defibrillation with rectangular pulse has been shown to require less peak current and less energy than is required for any other monophasic pulse shapes. In general, these studies indicate that energy stored at high electrical potential is more effective at defibrillating a heart than the same amount of energy stored at low electrical potential. Further, it has been shown that long, low amplitude tails on the pulse are detrimental to defibrillation.

As capacitors in a defibrillator must today store up to 40 joules, the size they occupy is generally large and they are difficult to package in a small implantable device. Multilayer ceramic capacitors have not been considered for high energy storage applications, even though some exhibit very large dielectric constants. Such high voltage multilayer ceramic capacitors, in large sizes, have been expensive specialty items and their total energy per unit volume is not nearly as high as in electrolytic capacitors. Recently, fabrication technologies for multilayer ceramic capacitors have improved significantly, permitting both substantially higher energy densities and lower costs.

To achieve acceptable performance for a capacitor in a defibrillator, its energy discharge capacitors must be able, for example, to withstand an applied voltage of approximately 800 volts, exhibit a capacitance of approximately 50 to 150 microfarads and occupy a volume of less than 20 cubic centimeters. An energy storage capacity up to 40 joules is required. Ferroelectric ceramics, while having extremely high dielectric constant values at low electric fields, exhibit a significant fall off in capacitance with increasing levels of applied electric field. In fact, at high field values, the exhibited capacitance can be as little as 10% of that at low dc field values. That is, conventional ferroelectric capacitors store a larger portion of their total charge at low voltage as compared with linear dielectric capacitors which maintain a constant capacitance independent of applied voltage. Lastly, ferroelectric materials can also show a substantial hysteresis loss in the charge/discharge, characteristic.

A class of ceramic materials, termed antiferroelectrics, exhibit increasing dielectric constant as electric fields are increased. With further increase in the electric field antiferroelectrics undergo a phase transition to a ferroelectric phase and then show a similar decrease in dielectric constant as is shown by conventional ferroelectrics.

It is an object of this invention to provide an improved, implantable cardiac defibrillator.

It is another object of this invention to provide an improved storage capacitor for use in an implantable cardiac defibrillator.

It is yet another object of this invention to provide an improved capacitor for an implantable cardiac defibrillator wherein the capacitor occupies less volume than prior art capacitors.

SUMMARY OF THE INVENTION

A cardiac defibrillator which incorporates the invention hereof includes a multilayer capacitor with a plurality of conductive electrodes and interspersed dielectric layers, each dielectric layer composed of constituents which cause the dielectric layer to exhibit antiferroelectric characteristics. The defibrillator includes a charging circuit for applying to the capacitor an electric field across each dielectric layer that is approximately $E_f$, where $E_f$ is a field value that causes the dielectric layer to make a transition to a ferroelectric phase. $E_f$ is selected, together with the capacitor dielectric thickness, such that the ferroelectric transition occurs near the maximum desired voltage of the output pulse. A preferred dielectric material comprises lead, lanthanum, zirconium and titanium, all at constituent values which cause the resulting ceramic material to lie within the antiferroelectric region.

DETAILED DESCRIPTION OF THE INVENTION

Requirements placed upon a capacitor operating in an implantable cardiac defibrillator are (1) that it have an effective operating voltage for the particular electrode system applied to the heart, (2) that it have the capacity to store up to 40 joules, (3) that its discharge rate enable the release of a majority of its stored energy within a 1 to 20 millisecond time period, and (4) that it occupy a small volume. As further indicated above, antiferroelectric materials have not been favored for capacitor applications due to their poor energy storage characteristics at low voltages. However, Applicant has determined that a wide class of antiferroelectric materials exhibit a particular characteristic which matches energy storage requirements of a cardiac defibrillator.

Figure 1:
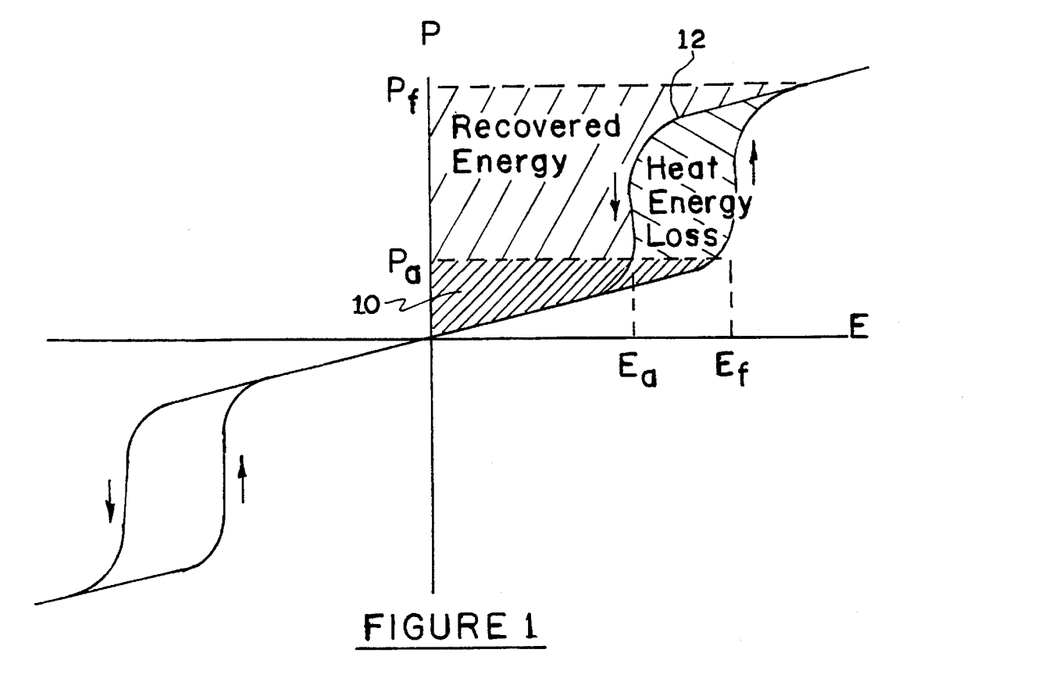
FIG. 1 is a plot of Polarization P versus Electric Field E for an antiferroelectric material.

Antiferroelectric crystalline materials exhibit structural phase changes, anomalies in dielectric permittivity, and other properties similar to ferroelectrics. However, antiferroelectric materials have zero net switchable dipole moment per unit cell, and consequently they exhibit no macroscopic polarization hysteresis in their low signal region. Because of the lack of macroscopic remnant polarization, so long as an antiferroelectric dielectric is maintained in its low voltage region, it experiences no hysteresis loss. However, as shown in FIG. 1, antiferroelectric dielectrics have a ferroelectric phase which can be induced by application of an electric field of sufficient magnitude. The threshold field required to induce a ferroelectric phase is designated $E_f$. If, after field-inducing the ferroelectric phase, the magnitude of the applied electric field is reduced, the dielectric material returns to its initial antiferroelectric phase. The field at which the latter transition occurs is designated $E_a$.

In FIG. 1, electric field E is plotted against polarization P for an antiferroelectric material. While all antiferroelectrics exhibit a characteristic such as that shown in FIG. 1, the shape of the characteristic varies widely, in dependence upon the constituents of the antiferroelectric dielectric. As can be seen from the plot, during lower levels of an applied electric field, the polarization is substantially linear with applied electric field. The shaded area 10 is proportional to the energy stored when the applied electric field is $E_f$. At the $E_f$ transition, (antiferroelectric-to-ferroelectric), the dielectric constant of the material increases significantly, thus facilitating a large energy storage (i.e. polarization) capability with only a small increase in applied electric field—a phenomenon not seen in linear capacitors. As a result, the amount of energy stored increases rapidly until the polarization reaches point $P_f$ where the energy storage characteristic becomes linear again. Upon discharge, the return curve 12 exhibits a hysteretic effect with the energy within the hysteresis region being lost as heat. Nevertheless, it is to be noted that the energy from $P_a$ to $P_f$ is recovered while the dielectric maintains a constant voltage and until the discharge curve reaches the ferroelectric-to-antiferroelectric transition field $E_a$.

In a capacitor, the applied voltages which cause electric fields $E_a$ and $E_f$ can be tailored by appropriate dimensioning of the dielectric layer thicknesses. It is generally desirable to have $E_a$ as close as possible to $E_f$ to increase the electric field to discharge efficiency and to reduce heat losses during a charge/discharge cycle. In a wide range of antiferroelectrics, $E_f$ can be set so that the voltage at which the transition occurs can be tailored to the specific needs of the patient. Thus, for a capacitor charged to a polarization level of about $P_f$, upon discharge, most stored energy has been released when $P_a$ is reached. This energy release occurs at a high electric potential. It is that feature which has been found to match the requirements of an implantable cardiac defibrillator.

Figure 2:
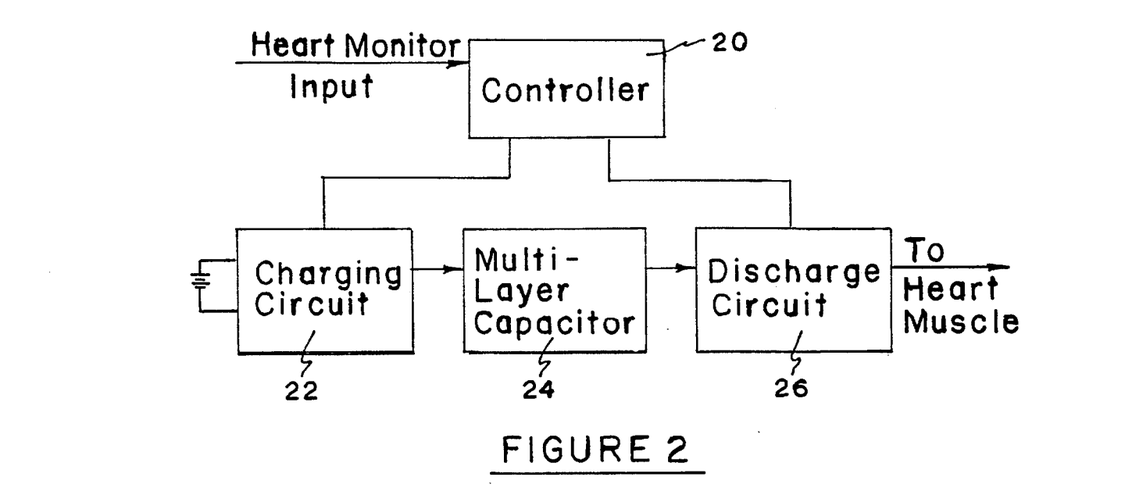
FIG. 2 is a high level block diagram of an implantable cardiac defibrillator.

Referring to FIG. 2, a block diagram is illustrated of an implantable cardiac defibrillator that employs a multilayer antiferroelectric ceramic capacitor. A controller 20 monitors the heart action and, upon determining that an tachyarrhythmic condition is occurring, causes a charging circuit 22 to charge multilayer capacitor 24 to a high voltage. While certain heart arrhythmias only require a small applied voltage to correct the arrhythmia, should a ventricular fibrillation occur, a high energy voltage pulse must be applied to the heart muscle to cause a desired conversion back to a sinus rhythm. At such time, controller 20 causes charging circuit 22 to charge multilayer capacitor 24 up to a programmed setting as high as its maximum (e.g., 700–800 volts). When the charge cycle is complete, controller 20 enables discharge circuit 26 to discharge the energy to the cardiac muscle. For further details of a cardiac defibrillator see U.S. Pat. No. 5,163,427 to Keimel, the disclosure of which is incorporated herein by reference.

As indicated in FIG. 1, the voltage applied by charging circuit 22 to multilayer capacitor 24 should preferably cause the electric field to slightly exceed the value $E_f$ for the particular antiferroelectric dielectric employed in capacitor 24 to take advantage of the large energy storage capability at this value. Following the work of Schuder et al. (1966) and Kroll (1993), it has been shown that "for effective ventricular defibrillation, that long, low amplitude tails on shocks are detrimental". Therefore, the discharge pulses, which typically follow an exponential decay $I=I_o e^{-t/RC}$, are usually truncated at approximately t=RC, where R=50 Ω is the resistance of the chest, C is the capacitance and $I_o$ is the initial charging current $I_o=V_{max}/R$. It can thus be seen that only the electrical energy stored at the upper ⅔ range of voltage is preferably used in defibrillation.

Figure 3:
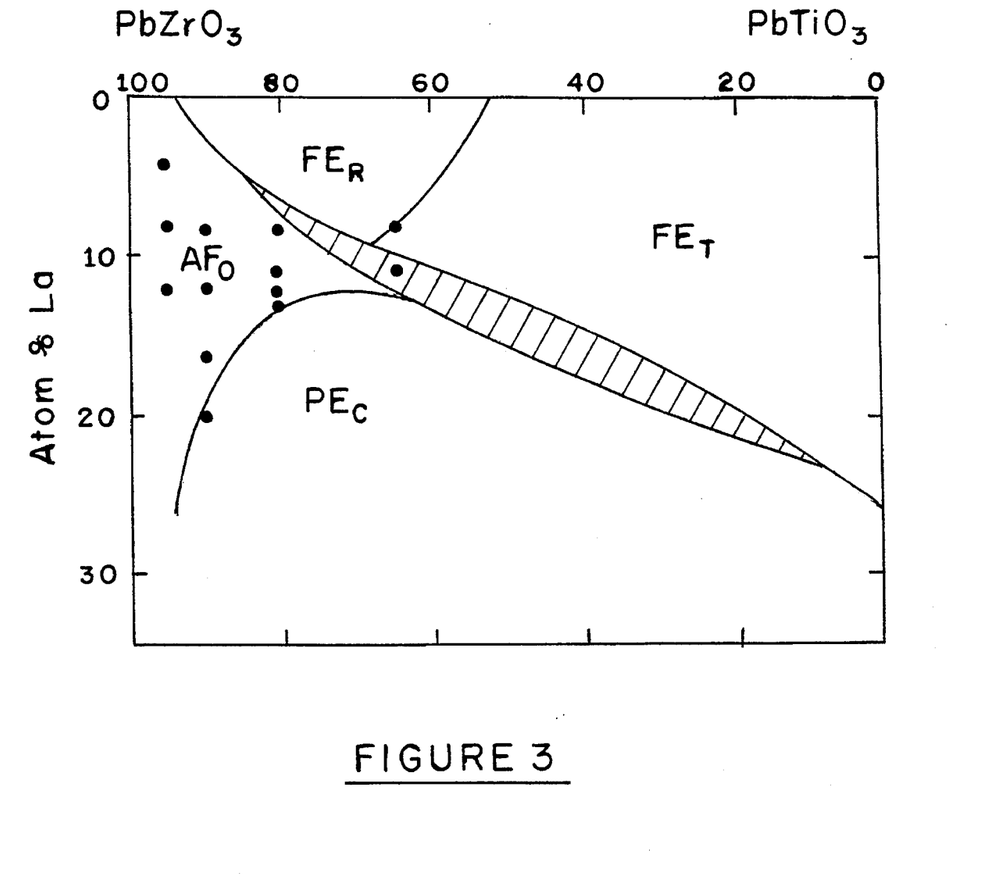
FIG. 3 is a phase diagram for various PLZT compositions.
Figure 4:
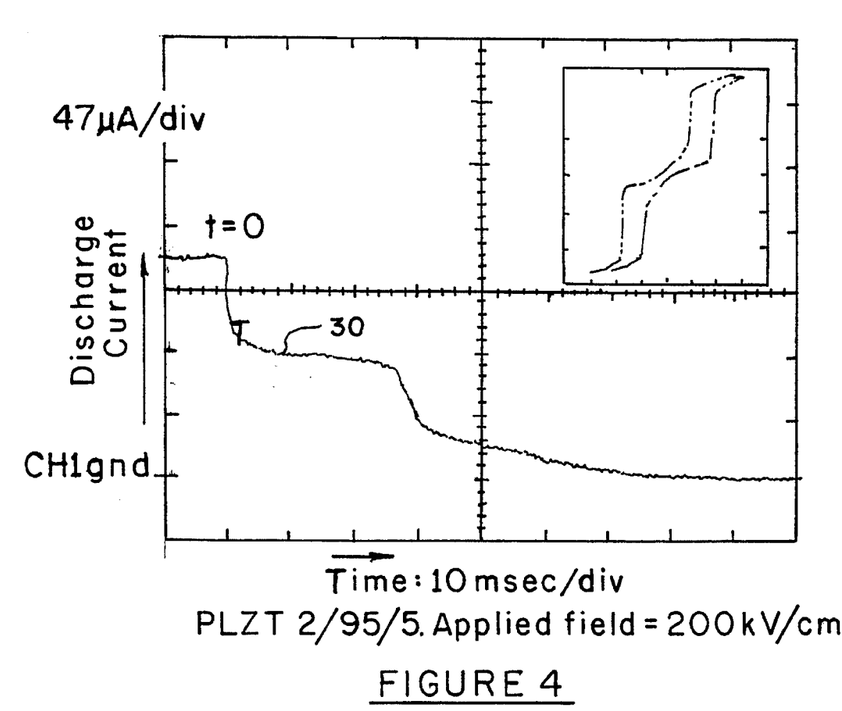
FIG. 4 is a plot of discharge current versus time for PLZT 2/95/5.
Figure 5:
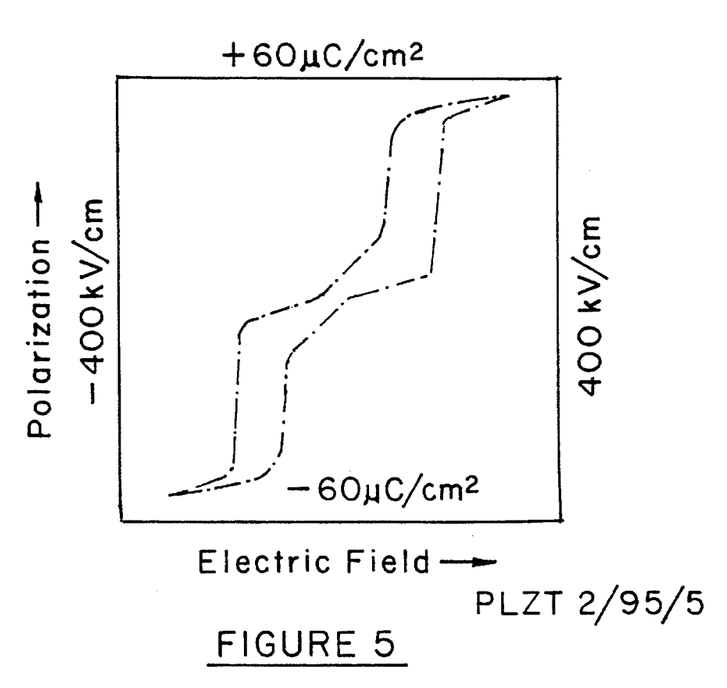
FIG. 5 is a plot of polarization versus electric field for the PLZT 2/95/5.
Figure 6:
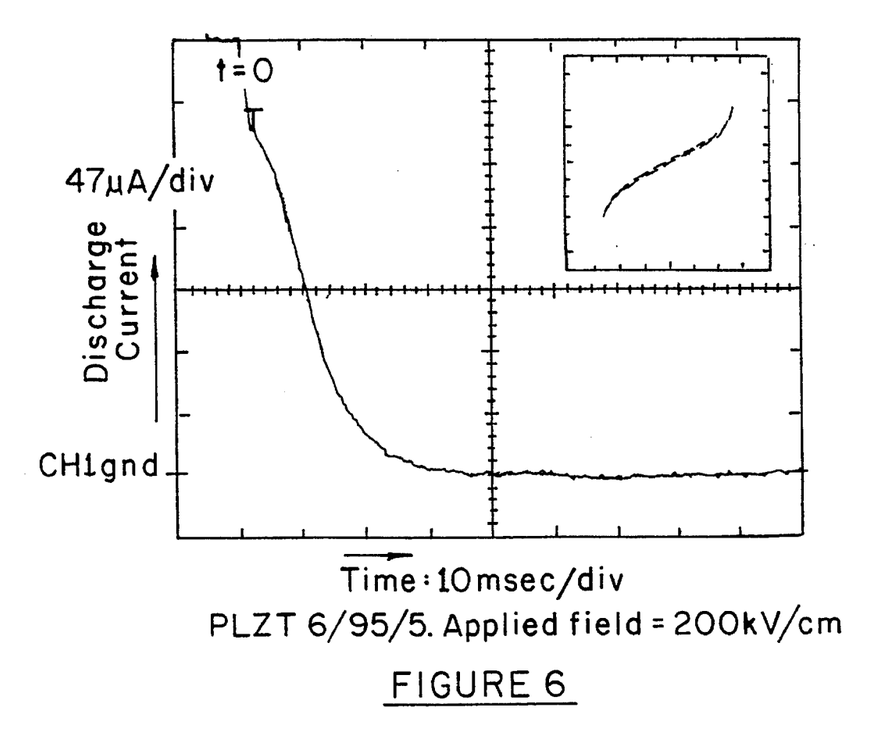
FIG. 6 is a plot of discharge current versus time for PLZT 6/95/5.
Figure 7:
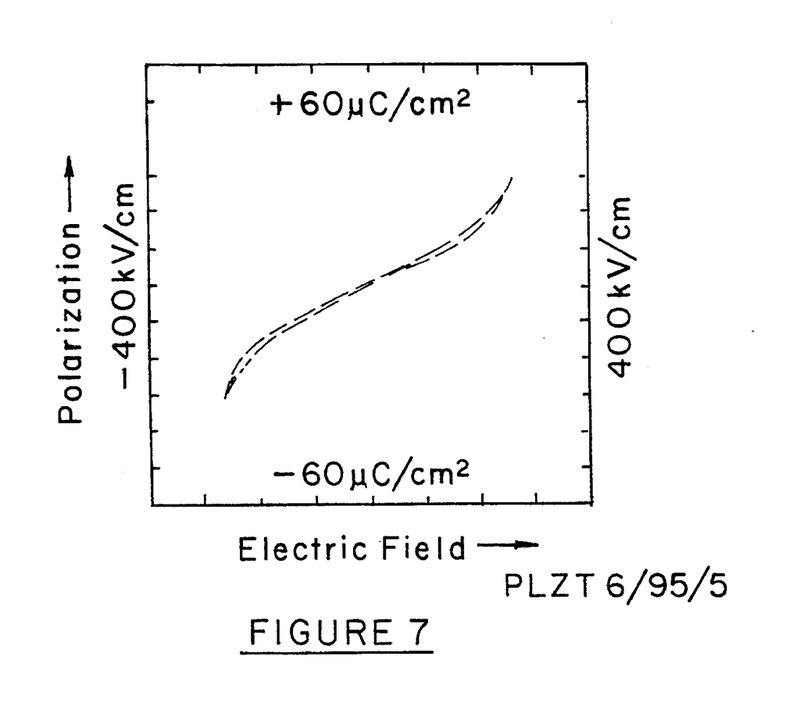
FIG. 7 is a plot of polarization versus electric field for the PLZT 6/95/5.
Figure 8:
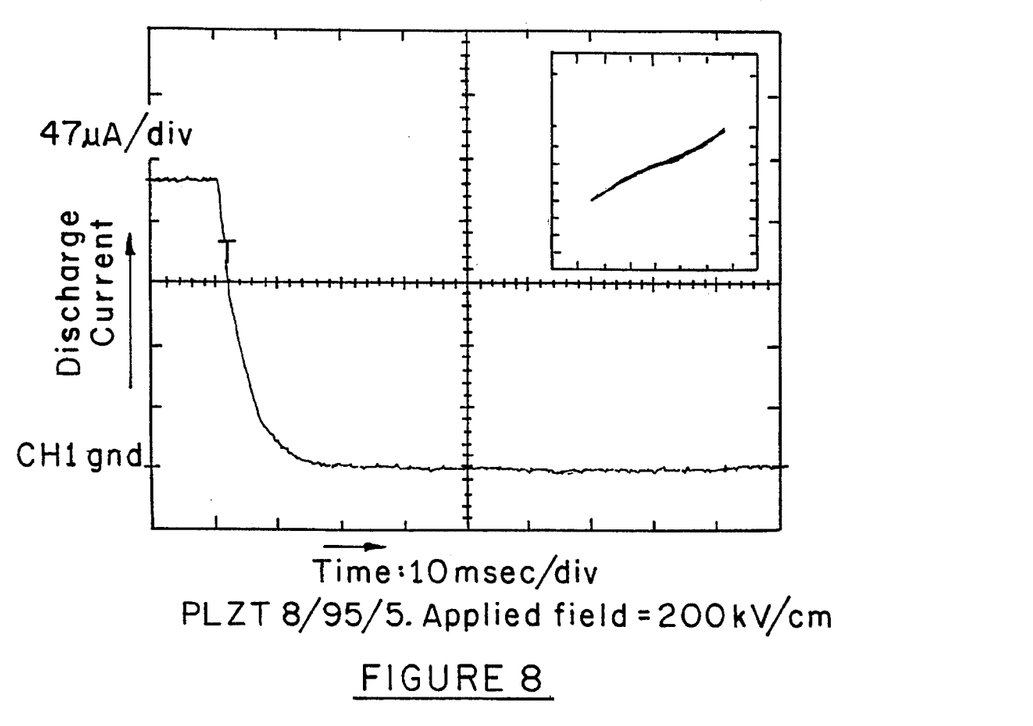
FIG. 8 is a plot of discharge current versus time for PLZT 8/95/5.
Figure 9:
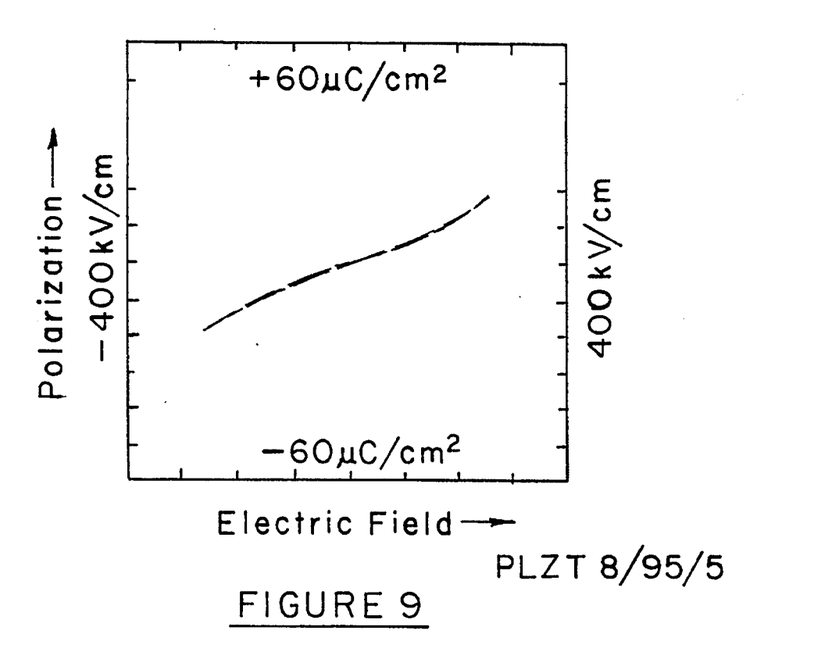
FIG. 9 is a plot of polarization versus electric field for the PLZT 8/95/5.

Referring now to FIG. 3, a phase diagram of a preferred antiferroelectric ceramic material is illustrated. The phase diagram shown in FIG. 3 is for various compositions of lead, lanthanum, zirconates and titanates (PLZT). The region designated $AF_O$ is the antiferroelectric region wherein the compositions exhibit an orthorhombic crystal structure. The region designated $FE_R$ is the ferroelectric region wherein the ceramic compositions exhibit a rhombohedral crystal structure. The area designated $FE_T$ is also a ferroelectric region wherein the material exhibits a tetragonal crystalline structure. The regions designated $PE_C$ and the shaded area exhibit paraelectric, cubic structure and relaxor ferroelectric-like dielectric properties, respectively. The dots in the phase diagram represents certain compositions that were evaluated in arriving at this invention.

As indicated, a capacitor for use with an implantable defibrillator has stringent imposed requirements which include an operating voltage up to 800 volts, a capacitance of approximately 50 to 150 microfarads, and a volume of approximately 20 cubic centimeters (or less). Assuming a voltage value of 800 volts and an achievable breakdown strength of 2000 volts/mil, the breakdown strength of the capacitor's dielectric is 80 volts per micron. To achieve an operating voltage rating of 800 volts, the thickness of the dielectric must at least equal 10 microns. Using the capacitance and volume specifications, the minimum dielectric constant K for a linear capacitor can be calculated as follows:

$$K = \frac{C \cdot t^2}{\epsilon_o (At)} \quad (1)$$

where At=volume (m$^3$)

$\epsilon_o$=8.854×10$^{-12}$ Farads/meter

A=capacitor surface area (m$^2$)

t=thickness of the dielectric (m)

C=capacitance (Farads)

The precise design of a nonlinear capacitor will, of course, depend upon the average K value for the specifically chosen antiferroelectric, as calculated over the total voltage and electric field range.

PLZT compositions in the x/95/5 and x/90/10 families were tested to determine their suitability for the defibrillator application. The "x" value indicates the lanthanum molar percent; the "95" (and "90") indicate the zirconium molar percent; and the "5" (and "10") indicate the titanium molar percent. The lead molar percent is equal to 100 minus the lanthanum molar percent. The results of the tests of certain antiferroelectric family compositions are summarized in Table 1.

TABLE 1

| Composition | # | Applied field (kV/cm) | Energy on discharge (Joules/cm$^3$) |
|---|---|---|---|
| PLZT 2/95/5 | 5 | 150 | 3.0 ± 0.025 |
| PLZT 2/95/5 | 1 | 200 | 4.0 |
| PLZT 2/95/5 | 1 | 320 | |
| PLZT 6/95/5 | 6 | 200 | 2.76 ± 0.44 |
| PLZT 6/95/5 | 5 | 260 | 4.81 ± 0.32 |
| PLZT 6/95/5 | 4 | 300 | 6.05 ± 0.57 |
| PLZT 8/95/5 | 5 | 200 | 1.6 ± 0.14 |
| PLZT 8/95/5 | 1 | 250 | 2.5 |
| PLZT 8/95/5 | 1 | 265 | |
| PLZT 8/95/5 | 2 | 300 | 4.6 |
| PLZT 8/95/5 | 1 | 350 | 5.5 |
| PLZT 4/90/10 | 5 | 200 | 1.1 ± 0.1 |
| PLZT 4/90/10 | 1 | 250 | 1.7 |
| PLZT 6/90/10 | 1 | 100 | 1.6 |
| PLZT 6/90/10 | 1 | 200 | 2.9 |

The first column in Table 1 identifies the specific composition that was tested, the second column the number of samples tested, the third column the applied field which was achieved (without breakdown) and the fourth column, the measured energy density on discharge. PLZT 8/95/5 provide evidence of an energy density on discharge of 5.5 joules/cc at 350 kV/cm. This field level indicates that a capacitor can be designed with layers having a thickness of approximately 20 microns. The PLZT 6/95/5 composition also yields an excellent average density of 6.05 J/cc at 300 kV/cm. At 200 kV/cm the PLZT 6/95/5 composition delivers only 2.2 J/cc because it has not gone through the antiferroelectric-to-ferroelectric transition $E_f$ at this applied field level. It is that transition, as described above, which causes the dielectric constant of the material to increase significantly, thus facilitating a large energy storage capability at this narrow range of electric fields.

FIGS. 4, 6, 8, 10 and 12 display discharge characteristics for the PLZT compositions listed in Table 1. In those FIGS. are shown plots of discharge current versus time for the specifically tested PLZT compositions being discharged into a fixed resistor. In each case, the applied field was 200 kV/cm. In the upper right hand corner of each of the respective Figs., the corresponding hysteresis curve is indicated. In FIGS. 5, 7, 9, 11 and 13, expanded views of the hysteresis curves are shown (i.e. plots of electric field versus polarization for the indicated PLZT compositions). The antiferroelectric-to-ferroelectric transition is readily seen in FIG. 4 wherein flat area 30 of the current versus time curve provides, what is in effect, a constant voltage source for a significant length of time.

Figure 10:
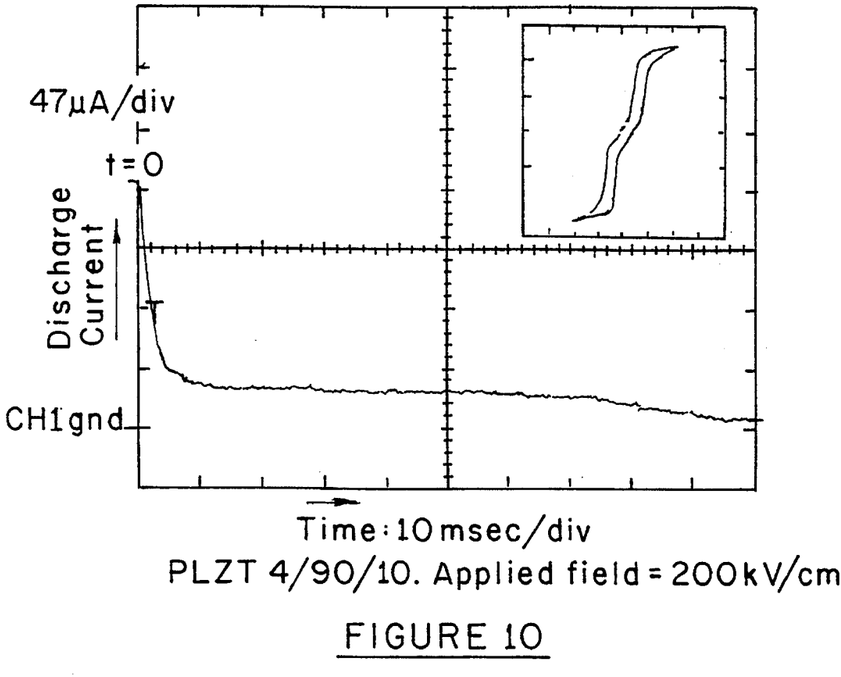
FIG. 10 is a plot of discharge current versus time for PLZT 4/90/5.
Figure 11:
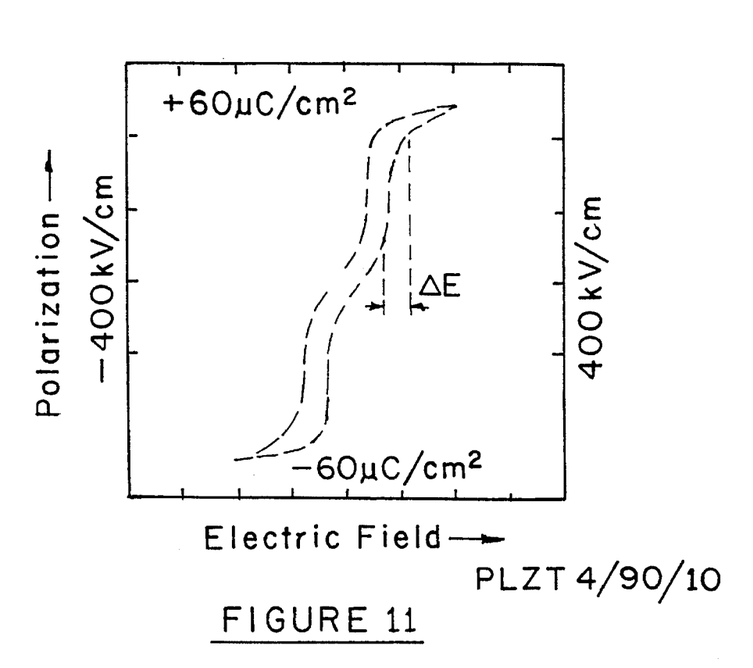
FIG. 11 is a plot of polarization versus electric field for the PLZT 4/90/5.
Figure 12:
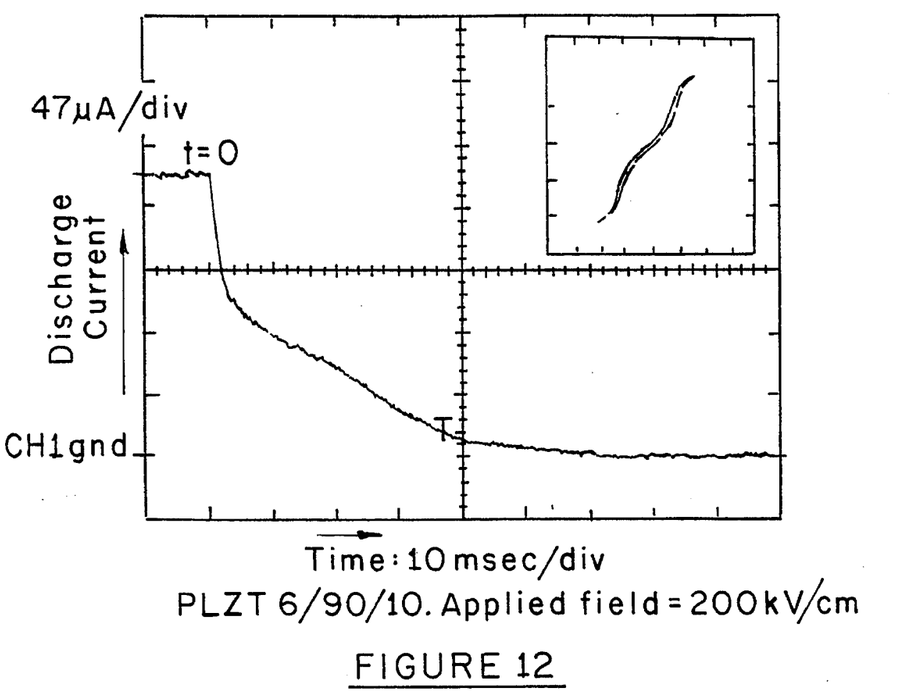
FIG. 12 is a plot of discharge current versus time for PLZT 6/90/5.
Figure 13:
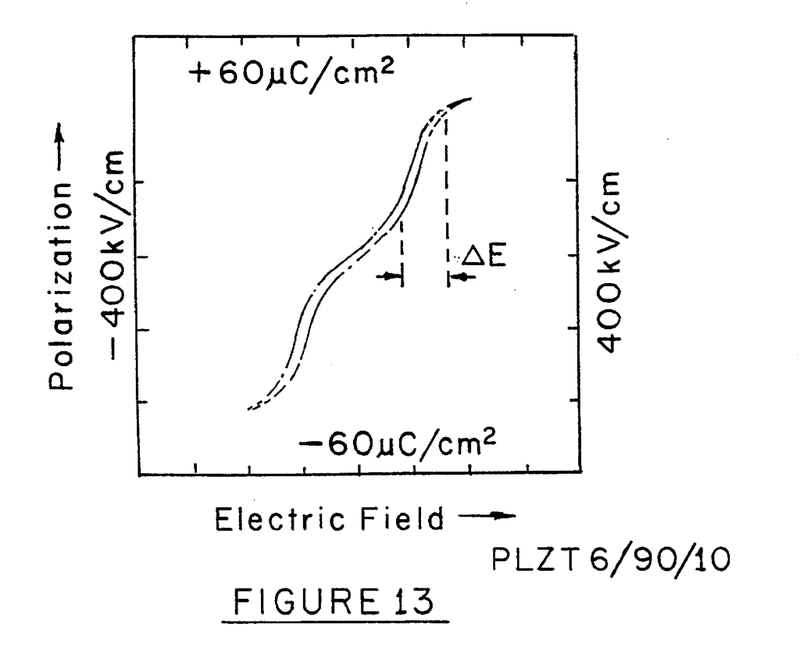
FIG. 13 is a plot of polarization versus electric field for the PLZT 6/90/5.

In FIG. 10, it can be seen that the time at constant current can exceed 70 milliseconds (in the case of PLZT 4/90/10). This region corresponds to the point at which the PLZT material loses charge (or polarization) at almost a constant voltage. This effect is best observed from the hysteresis loops shown in FIG. 5 (PLZT 2/95/5), FIG. 11 (PLZT 4/90/10) and FIG. 13 (PLZT 6/90/10). In FIG. 11 ΔE is the field change which corresponds to portion of the discharge characteristic which provides a nearly constant voltage source.

PLZT 8/95/5 (see FIG. 9) does not show this pure constant linear voltage behavior, though it provides a sufficiently high value of average voltage over a discharge time to be superior to a linear capacitor used for defibrillation purposes.

The negative aspect of the rapid reduction of polarization with decreasing electric field on discharge (for compositions indicating a sharp antiferroelectric-to-ferroelectric transition) is the sudden strain change experienced in the substrate. It is for this reason that PLZT composition 8/95/5 may be preferable over compositions with a lower lanthanum content. However, for less stringent voltage applications, the lower lanthanum content PLZT compositions are useful.

While the PLZT x/90/10 family falls short of the energy densities exhibited by the PLZT x/95/5 family, they still provide substantial energy density storage capabilities. In view of their slim-hysteresis loops, the PLZT x/90/10 family materials indicate better efficiencies than the PLZT x/95/5 family.

In summary, a variety of PLZT compositions have been tested and found applicable for use as dielectric materials in capacitors used with defibrillators. While a number of PLZT compositions which fall within the antiferroelectric region have been tested, other compositions which exhibit antiferroelectric properties will also exhibit the characteristic of high energy release at upper voltage reaches of the charge/discharge characteristic. As has been shown by Schuder et al. and Kroll, the energy released at higher voltages, which makes the current pulse more closely resemble a square wave, has been shown experimentally to be more effective for defibrillation. For instance, PbSnZrTi and PbBaLaZrTi both exhibit antiferroelectric characteristics. In any case, it is critical that the applied voltage across the antiferroelectric material cause the material to transition (either fully or at least partially) between its ferroelectric and antiferroelectric phase states. It is this transition which enables the extraordinarily large discharge of energy to occur at upper voltage reaches of the charge/discharge characteristic.

While it can be seen from the above data that certain PLZT compositions are particularly useful in the defibrillator application, a wide variation of constituents in the ultimate PLZT composition is also within the preferred range. That range extends from PLZT compositions exhibiting 2/95/5 to 3/92.5/7.5 to 4/90/10 to 10/90/10. Further, the range encompasses PLZT compositions between 2/95/5 and 10/95/5 and from 10/95/5 to 10/90/10. Thus PLZT composition may exhibit a La molar percentage extending from approximately 2 to 10, a Zr molar percentage of approximately from 90 to 95 and a Ti molar percentage of approximately from 5 to 10.

It should be understood that the foregoing description is only illustrative of the invention. Various alternatives and modifications can be devised by those skilled in the art without departing from the invention. For instance one skilled in the art will realize that further compositions can fulfill the needs described here. Tin can be substituted for zirconium in the PLZT compositions. Antiferroelectric behavior of compositions holding up to 50 mole % tin replaced zirconium have been reported. Barium can be substituted for lead in the PLZT compositions. Barium substitution should be limited to 10 mole %. Accordingly, the present invention is intended to embrace all such alternatives, modifications and variances which fall within the scope of the appended claims.

The invention claimed is:

1. A cardiac defibrillator for applying a high energy, short duration electrical pulse to the heart muscle, said defibrillator comprising:

capacitor means comprising plural dielectric layers, each layer composed of constituents which exhibit both an antiferroelectric phase and a ferroelectric phase in dependence upon an applied electric field; and charging circuit means for applying to said capacitor means, a voltage which causes an electric field at least equal to $E_f$ to appear across said dielectric layers, where $E_f$ is a field value which causes said dielectric layers to transition at least partially from said anti-ferroelectric phase to said ferroelectric phase; and discharge means for applying energy stored in said capacitor means to a heart muscle.

2. A cardiac defibrillator as recited in claim 1, wherein each said dielectric layer comprises lead, lanthanum, zirconium and titanium (PLZT) constituents.

3. The cardiac defibrillator as recited in claim 2 wherein the lanthanum, zirconium and titanium constituents are present in the PLZT in molar percentages as follows:

La: from approximately 2 to approximately 10,

Zr: from approximately 90 to approximately 95, and

Ti: from approximately 5 to approximately 10.

4. The cardiac defibrillator as recited in claim 2 wherein the zirconium and titanium constituents are present in the PLZT in molar percentages of approximately 95 and 5, respectively.

5. The cardiac defibrillator as recited in claim 2 wherein the zirconium and titanium constituents are present in the PLZT in molar percentages of approximately 90 and 10, respectively.

6. A cardiac defibrillator as recited in claim 1, wherein each said dielectric layer comprises lead, lanthanum, tin and titanium constituents.

7. A cardiac defibrillator as recited in claim 1, wherein each said dielectric layer comprises barium, lanthanum, zirconium and titanium constituents.

8. The cardiac defibrillator as recited in claim 7 wherein the barium constituent molar percentage does not exceed approximately 10%.

\* \* \* \* \*